United States Patent [19]
Pellacini et al.

[11] Patent Number: 6,166,051
[45] Date of Patent: Dec. 26, 2000

[54] THIOL DERIVATIVES WITH METALLOPEPTIDASE (ACE/NEP) INHIBITORY ACTIVITY

[75] Inventors: Franco Pellacini, Milan; Stefano Romagnano, Buccinasco; Gabriele Norcini, Vizzola Ticino; Francesco Santangelo, Milan; Claudio Semeraro, Bresso, all of Italy

[73] Assignee: Zambon Group S.p.A., Vicenza, Italy

[21] Appl. No.: 09/091,415

[22] PCT Filed: Dec. 9, 1996

[86] PCT No.: PCT/EP96/05496

§ 371 Date: Jun. 23, 1998

§ 102(e) Date: Jun. 23, 1998

[87] PCT Pub. No.: WO97/24341

PCT Pub. Date: Jul. 10, 1997

[30] Foreign Application Priority Data

Dec. 28, 1995 [IT] Italy .................. MI95A02772

[51] Int. Cl.$^7$ .................. A61K 31/44; A61K 31/426; C07D 213/04
[52] U.S. Cl. .................. 514/357; 546/335; 546/337; 548/203; 548/204; 548/205; 549/77; 514/365; 514/438

[58] Field of Search .................. 514/357, 365, 514/438; 546/335, 337; 548/203, 204, 205; 549/77

[56] References Cited

U.S. PATENT DOCUMENTS 5,414,013   5/1995   Delaney et al. .................. 514/423

*Primary Examiner*—C. S. Aulakh
*Attorney, Agent, or Firm*—Arent, Fox, Kintner, Plotkin, Kahn

[57] ABSTRACT

Compounds of formula (I) wherein R, $R_1$, $R_2$, $R_3$ have the meanings reported in the description, processes for their preparation and pharmaceutical compositions which contain them as active ingredients are described. The compounds of formula (I) are endowed with a mixed ACE-inhibitory and NEP-inhibitory activity and are useful in the treatment of cardiovascular diseases.

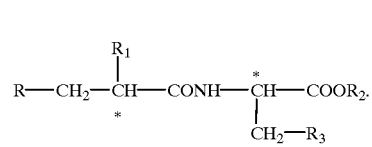

12 Claims, No Drawings

THIOL DERIVATIVES WITH METALLOPEPTIDASE (ACE/NEP) INHIBITORY ACTIVITY

This application is a 371 application of PCT/EP96/05496, filed Dec. 9, 1996.

The present invention relates to thiol derivatives with metallopeptidase inhibitory activity and, more particularly, it relates to N-mercaptoacyl alanine derivatives useful in the treatment of cardiovascular diseases.

The pharmacologic interest towards the study of metallopeptidase inhibitory molecules derives from the role that said enzymes exert on the level of the cardiocirculatory system.

It is well-known in fact that compounds with angiotensin converting enzyme (ACE) inhibitory activity are mainly useful in the treatment of hypertension. heart failure and post-infarct in that they inhibit the formation of angiotensin II, a substance which comprises several effects among which the increase of the blood pressure.

Compounds with endothelin converting enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase enzyme (NEP), also called enkephalinase. are useful as vasodilators in that the NEP enzyme is responsible for the inactivation, not only of endogenous enkephaline, but also of some natriuretic factors among which, for instance. the atrial factor (ANF), a hormone secreted by heart which increases the vasodilation and, on the renal level increases diuresis and natriuresis.

Therefore, even exerting their action on the cardiovascular system with different mechanisms of action, the compounds with metallopeptidase inhibitory activity are generally used, alone or in combination among them, in the treatment of hypertension, renal failure, congestive heart failure and ischemic cardiopathies.

Among the thiol derivatives inhibitors of metallopeptidases, Thiorphan [(DL-(3-mer-capto-2-benzylpropanoyl)glycine], described for the first time by Roques et al. in Nature, Vol. 288, pages 286–288, (1980), and Captopril (The Merck Index, XI ed., No. 1773, page 267) are considered the parent compounds for NEP-inhibitors and ACE-inhibitors, respectively.

Other molecules having a thiol structure endowed with metallopeptidase inhibitory activity were described in the literature.

N-mercaptoacyl dipeptides endowed with ECE-inhibitory activity and, more particularly, N-mercaptoacyl derivatives of triptophan were described by S. R. Bertenshaw et al. in Bioorganic & Medicinal Chemistry Letters, 10, 1953–1958, 1993.

U.S. Pat. No. 4,401,677 (E.R. Squibb & Sons, Inc.) describes mercaptoalkanoyl amino acids endowed with enkephalinase inhibitory activity.

U.S. Pat. No. 4,199,512 (E.R. Squibb & Sons. Inc.) describes mercaptoalkanoyl amino acids endowed with ACE-inhibitory activity.

The European patent application No. 0566157 (Schering Corporation) describes N-mercaptoacyl derivatives of alanine endowed with NEP-inhibitory activity.

The European patent application No. 0449523 (E.R. Squibb & Sons, Inc.) describes mercapto or acylthio trifluoromethylamides with NEP-inhibitory activity.

The European patent application No. 0524553 [Institut National de la Santè et de la Recherche Mèdicale (INSERM)] describes acylmercaptoalkanoyldipeptides endowed with neutral endopeptidase and peptidylpeptidase A inhibitory activity.

The international patent application No. WO 93/08162 [Rhone-Poulenc Rorer S.A.—Institut National de la Santè et de la Recherche Mèdicale (INSERM)] describes β,β-disubstituted α-mercaptomethylpropionylamides endowed with mixed ACE/NEP inhibitory activity.

The European patent application No. 0419327 (Societè Civile Bioproject) describes amino acid derivatives such as, for instance, N-mercaptoacyl derivatives of phenylalanine, stydine and triptophan, endowed with enkephalinase and ACE inhibitory activity.

α-Mercaptoacyl dipeptides endowed with ACE-inhibitory and NEP-inhibitory activity were also described by S. S. Bhagwat et al. in Bioorganic & Medicinal Chemistry Letters, 7, 735–738, 1995.

In this last work the authors conclude that, while the presence of a biphenylmethyl group confers an interesting mixed ACE/NEP-inhibitory activity at the molecules having an α-mercaptoacyl dipeptide structure, the substitution of the biphenyl group with groups such as α- or β-naphthyl causes a significant loss of activity.

Now we have found N-mercaptoacyl alanine derivatives which are endowed with a remarkable inhibitory activity on the angiotensin converting enzyme as well as on the neutral endopeptidase enzyme (dual ACE/NEP-inhibitory activity) which renders them particularly useful in the therapy of cardiovascular pathologies.

Therefore object of the present invention are the compounds of formula $$R-CH_2-\underset{\underset{*}{|}}{\overset{R_1}{\overset{|}{C}H}}-CONH-\overset{*}{\underset{\underset{CH_2-R_3}{|}}{\overset{|}{C}H}}-COOR_2 \quad (I)$$

wherein

R is a mercapto group or a $R_4COS$ group convertible in the organism to mercapto group;

$R_1$ is a straight or branched $C_2$–$C_4$ alkyl group or an aryl or arylalkyl group with from 1 to 6 carbon atoms in the alkyl moiety wherein the aryl is a phenyl or a 5 or 6 membered aromatic heterocycle with one or two heteroatoms selected among nitrogen, oxygen and sulphur, optionally substituted with one or more substituents. the same or different, selected among halogen atoms, hydroxy groups, alkoxy, alkyl, alkylthio, alkylsulphonyl or alkoxycarbonyl groups with from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino or mono- or di-alkylaminocarbonyl groups with from 1 to 6 carbon atoms in the alkyl moiety;

$R_2$ is a hydrogen atorn, a straight or branched $C_1$–$C_4$ alkyl group or a benzyl group;

$R_3$ is a 5 or 6 membered aromatic heterocycle with one or two heteroatoms selected among nitrogen, oxygen and sulphur, optionally substituted with a phenyl group, being the phenyl and the heterocyclic group optionally substituted with one or more substituents, the same or different, selected among halogen atoms. alkyl alkoxy, alkylthio or alkoxycarbonyl groups with from 1 to 3 carbon atoms in the alkyl moiety;

$R_4$ is a straight or branched $C_1$–$C_4$ alkyl group or a phenyl group;

the carbon atoms marked with an asterisk are stereogenic centers;

and pharmaceutically acceptable salts thereof;

provided that $R_3$ is not an imidazolyl or indolyl group.

The compounds of formula I contain two stereogenic centers and can thus exist in the form of stereoisomers.

Therefore, object of the present invention are the compounds of formula I in the form of stereoisomeric mixture as well as in the form of single stereoisomers.

The compounds of formula I object of the present invention are endowed with a dual ACE/NEP-inhibitory activity and are useful in the treatment of cardiovascular diseases.

In the present description, unless otherwise specified, with the term straight or branched alkyl group we intend an alkyl such as methyl, ethyl, n.propyl isopropyl, n.butyl sec-butyl tert-butyl isobutyl n.pentyl 2-pentyl, 3-pentyl isopentyl tert-pentyl n.hexyl and isohexyl; with the term straight or branched alkoxy group we intend an alkoxy such as methoxy, ethoxy, n.propoxy and isopropoxy; with the term halogen atom we intend a fluorine, chlorine, bromine or iodine atom; with the term acyl we intend an acyl group deriving from an aliphatic or aromatic carboxylic acid such as acetic, propionic, butyric and benzoic acid; with the term 5 or 6 membered aromatic heterocycle containing 1 or 2 heteroatoms selected among nitrogen. oxygen and sulphur we intend a group such as thiazole, isoxazole, oxazole, isothiazole, pyrazole, imidazole, thiophene, pyrrole, pyridine, pyrimidine, pyrazine, pyridazine and furan, optionally benzocondensed.

Examples of pharmaceutically acceptable salts of the compounds of formula I are the salts with alkali or alkali-earth metals and the salts with pharmaceutically acceptable organic bases.

Preferred compounds of formula I are the compounds wherein $R_3$ is a 5 or 6 membered aromatic heterocyclic group with one or two heteroatoms selected among nitrogen, oxygen and sulphur.

Still more preferred compounds. in this class, are the compounds of formula I wherein $R_1$ represents a phenylalkyl group optionally substituted with one or more substituents. the same or different, selected among halogen atoms. hydroxy, alkyl or alkoxy groups.

Preferred examples of pharmaceutically acceptable salts of the compounds of formula I are the salts with alkali metals such as sodium, lithium and potassium.

It is clear to the man skilled in the art that the compounds of formula I wherein R is a $R_4$COS group convertible in the organism to mercapto group, as well as the compounds of formula I wherein $R_2$ is an alkyi or benzyl group, are biologic precursors (pro-drugs) of the corresponding compounds of formula I wherein R is a mercapto group (R=SH) or $R_2$ is a hydrogen atom ($R_2$=H), respectively.

Specific examples of preferred compounds of formula I, object of the present invention, are:

N-(3-phenylcarbonylthio-2-phenylmethylpropionyl)-(2-thienyl)-alanine methyl ester;

N-(3-phenylcarbonylthio-2-phenylmethylpropionyl)-(4-thiazolyl)-alanine methyl ester;

N-(3-phenylcarbonylthio-2-phenylmethylpropionyl)-(2-pyridyl)-alanine methyl ester;

N-(3-phenylcarbonylthio-2-phenybnethylpropionyl)-(3-pyridyl)-alanine methyl ester;

N-(3-phenylcarbonylthio-2-phenylnethylpropionyl-(2-furyl)-alanine methyl ester;

N-(2-phenylmethyl-3-mercaptopropionyl)-(2-thienyl)-alanine;

N-(2-phenylmethyl-3-mercaptopropionyl)-(4-thiazolyl)-alanine;

N-(2-phenylmethyl-3-mercaptopropionyl)-(2-pyridyl)-alanine;

N-(2-phenylmethyl-3-mercaptopropionyl)-(3-pyridyl)-alanine;

N-(2-phenylmethyl-3-mercaptopropionyl)-(2-furyl)-alanine.

The preparation of the compounds of formula I, object of the present invention, is carried out according to a synthetic process comprising the reaction between a compound of formula

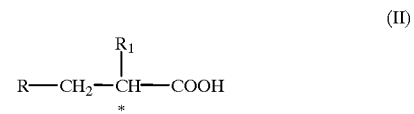
(II)

wherein

R and $R_1$ have the above reported meanings;

and an alanine derivative of formula

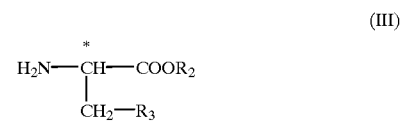
(III)

wherein $R_2$ and $R_3$ have the above reported meanings.

The condensation reaction is carried out according to conventional techniques of the chemistry of peptides.

Before carrying out the reaction it can be useful to properly protect the optional functional groups which could interfere in the reaction.

The optional protection is carried out according to conventional techniques.

In this respect the compounds wherein R is a $R_4$COS group are preferably used as intermediates of formula II, thus obtaining the corresponding compounds of formula I wherein R=$R_4$COS from which, by hydrolysis, the compounds of formula I wherein R=SH can be obtained.

The evaluation of the usefulness of the optional protection as well as the selection of the kind of adopted protection, according to the reaction to be carried out and to the functional groups to be protected, are within the normal knowledge of the man skilled in the art.

The removal of the optional protective groups is carried out according to conventional techniques.

For a general reference to the use of protective groups in organic chemistry see Theodora W. Greene and Peter G. M. Wuts "Protective Groups in Organic Synthesis", John Wiley & Sons, Inc., II Ed., 1991.

The compounds of formula II and III are known or easily prepared according to conventional methods.

As example, the compounds of formula II can be prepared as described in British patent No. 1576161 in the name of E.R. Squibb & Sons Inc.

The compounds of formula I in the form of single stereoisomers are prepared by stereoselective synthesis or by separation of the stereoisomeric mixture according to conventional techniques.

Also the preparation of the salts of the compounds of formula I, object of the present invention, is carried out according to conventional techniques.

The compounds of formula I, object of the present invention, are endowed with a dual ACE/NEP-inhibitory activity and are useful in the treatment of cardiovascular diseases.

The inhibitory activity of the compounds of formula I was evaluated by means of in vitro tests.

In particular, the inhibitory activity of the compounds of formula I was evaluated in comparison to the aforementioned Thiorphan and Captopril.

The in vitro inhibitory activity of the compounds of formula I, expressed as $IC_{50}$ value, is pharmacologically significant in that it results at nM concentrations.

Said activity resulted to be comparable to that of Captopril to what it concerns the ACE-inhibitory activity, and to that of Thiorphan. to what it concerns the NEP-inhibitory activity.

For a practical use in therapy, the compounds of formula I can be formulated in solid or liquid pharmaceutical compositions, suitable to oral or parenteral administration. Therefore, the pharmaceutical compositions containing a therapeutically effective amount of a compound of formula I in admixture with a carrier for pharmaceutical use are a further object of the present invention.

Specific examples of pharmaceutical compositions according to the present invention are tablets, coated tablets, capsules, granulates, solutions and suspensions suitable to oral administration, solutions and suspensions suitable to parenteral administration. The pharmaceutical compositions object of the present invention are prepared according to conventional techniques.

The daily dose of the compound of formula I or of the corresponding pro-drug will depend on several factors such as the seriousness of the disease, the individual response of the patient or the kind of formulation but it is usually comprised between 0.1 mg and 10 mg per kg of body weight divided into a single dose or into more daily doses.

With the aim of illustrating the present invention the following examples are now given.

Unless otherwise specified, the flash chromatographies were carried out by using flash chromatography silica gel from Baker company (code 7024-00).

EXAMPLE 1

Preparation of N-(3-phenylcarbonylthio-2-phenyimethyipropionyl)-(4-thiazolyl)-L-alanine Methyl Ester (compound 1)

A solution of hydroxybenzotriazole (1.25 g; 9.25 mmoles) in tetrahydrofuran (30 ml) and, subsequently, a solution of dicyclohexyicarbodiimide (1.81 g; 9.25 mmoles) in methylene chloride (10 ml) were added, at 0° C. under stirring, to a mixture formed by 3-phenylcarbonylthio-2-phenylnethylpropionic acid (2.78 g; 9.25 mmoles), (4-thiazolyl)-L-alanine methyl ester (2.40 g; 9.25 mmoles), obtained by treating N-tert-butoxycarbonyl-(4-thiazolyl)-L-alanine methyl ester (furnished by Sinthetech Inc., Oregon) with methanol and thionyl chloride, triethylamine (2.58 ml; 18.5 mmoles) in tetrahydrofuran (25 ml) and methylene chloride (40 ml).

The reaction mixture was kept under starring at room temperature for 20 hours, then dicyclohexylurea was filtered off and the solvent was evaporated at reduced pressure. The residue was collected with ethyl acetate and the solution was washed with an aqueous solution of sodium chloride at 20%, sodium bicarbonate at 5% and sodium chloride at 20% again.

After separation of the phases and evaporation of the organic phase, the resultant solid was purified by flash chromatography (silica gel, eluent ethyl acetate:hexane=1:1, pressure of nitrogen 0.1 atm) thus furnishing N-(3-phenylcarbonylthio-2-phenylmethylpropionyl)-(4-thiazolyl)-L-alanine methyl ester (3.85 g; 88% yield) as an oily product.

By treatment of the oily product with ethyl ether and hexane and by subsequent filtration, the desired product was obtained as a solid (2.2 g; stereoisomeric ratio 2S:2R=85:15).

$^1$H-NMR (200 MHz, CDCl$_3$): δ (ppm): 2.67–3.30 (m, 7H, CH$_2$—CH—CH$_2$, C$\underline{H}_2$-thiazolyl); 3.60 (s, 3H, OCH$_3$); 4.77–4.89 (m, 1H, CONH—C$\underline{H}$); 6.53 (s, 1H NH); 7.15–7.90 (m, 10H, phenyl); 6.92–8.51(m, 2H, thiazoliyl).

From mother liqueurs a further fraction of the compound 1 was isolated (1.5 g; stereoisomeric ratio 2S:2R=65:35), as an oily product.

By working in an analogous way the following compounds were prepared:

N-(3-phenylcarbonylthio-2-phenylmethylpropionyl)-(2-thienyl)-L-alanine Methyl Ester (compound 2)

m.p. 68–70° C.

$^1$H-NMR (200 MHz, CDCl$_3$): δ (ppm): 2.65–3.40 (m, 7H, CH$_2$—CH—CH$_2$, C$\underline{H}_2$-thienyl); 3.61 and 3.62 (2s, 3H, OCH$_3$); 4.70–4.90 (2m, 1H, CONH—C$\underline{H}$); 5.85–5.90 and 5.95–6.02 (2m, 1H, NH); 6.60–7.05 (m, 3H, thienyl); 7.10–8.00 (m, 10H, phenyl);

N-(3-phenylcarbonylthio-2-phenylmethylpropionyl)-(2-pyridyl)-L-alanine Methyl Ester (compound 3)

m.p. 84–86° C.

$^1$H-NMR (200 MHz, CDCl$_3$): δ (ppm): 2.70–3.30 (m, 7H, CH$_2$—CH—CH$_2$, C$\underline{H}_2$-pyridyl); 3.59 (s, 3H, OCH$_3$); 4.71–4.92 (m, 1H, CONH—CH); 6.90–8.28 (m, 15H, NH, phenyl, pyridyl).

EXAMPLE 2

Preparation of N-(2-phenylmethyl-3-mercaptopropionyl)-(4-thiazolyl)-L-alanine (compound 4)

N-(3-phenylcarbonylthio-2-phenylmethylpropionyl)-(4-thiazolyl)-L-alanine methyl ester (1.20 g; 2.56 mmoles), prepared as described in example 1, was suspended in ethanol (30 ml), degassed by nitrogen doubling to eliminate the oxygen.

An aqueous degassed solution of sodium hydroxide 1N (7.68 ml) was added, dropwise at 0° C. and under nitrogen, to the suspension.

The reaction mixture was kept under sting for 4 hours at room temperature, then cooled at 0° C. and acidified with a solution of hydrochloric acid 10% (5 ml) and water (5 ml), previously degassed.

The mixture was evaporated to dryness at reduced pressure and the residue was collected with acetonitrile and evaporated to dryness again.

The residue, collected with a methanol:methylene chloride=1:1 mixture (15 ml), was filtered to remove the inorganic salts and the solution was evaporated to dryness at reduced pressure.

The residue was then collected with water containing hydrochloric acid (20 ml) and methylene chloride (20 ml).

The phases were separated and the organic phase was evaporated to dryness at reduced pressure furnishing a residue (0.81 g) from which, by treatment with tert-butyl ether, filtration and drying, N-(2-phenylmethyl-3- mercaptopropionyl)-(4-thiazolyl)-L-alanine (0.52 g; 58% yield; stereoisomeric ratio 2S:2R=90:10) was obtained. m.p. 145–147° C.

$^1$H-NMR (200 MHz, CDCl$_3$): δ (ppm): 1.53 (t, 1H, JHH=8.4 Hz, SH); 2.51–2.98 (m, 5H, CH$_2$—CH—CH$_2$); 3.39–3.51 (ABX, 2H, Jab=14.7 Hz, Jax=3.4 Hz, Jbx=5.9 Hz, CH$_2$-thiazolyl); 4.63–4.71 (m, 1H, CHCOO); 6.51 (d, 1H, JHH=5.8 Hz, CONH); 7.09–7.30 [m, 6H, phenyl CH(thiazolyl)]; 8.85 [d, 1H, JHH=2.0 Hz, CH(thiazolyl)].

By working in an analogous way the following compounds were prepared:

N-(2-phenylmethyl-3-mercaptopropionyl)-(2-thienyl)-L-alanine (compound 5)

$^1$H-NMR (200 MHz, CDCl$_3$): δ (ppm): 1.40–1.61 (m, 1H, SH); 2.47–3.46 (m, 7H, CH$_2$—CH—CH$_2$, CH$_2$—CH—COO); 4.78–4.91 (m, 1H, CHCOO); 6.00–6.06 (m, 1H, CONH); 6.40–7.33 (m, 8H, aromatic); 7.50 (bs, 1H, COOH);

N-($^2$-phenylmethyl-3-mercaptopropionyl)-(2-pyridyl)-L-alanine (compound 6)

m.p. 164–166° C.

$^1$H-NMR (200 MHz, DMSO-d$_6$): δ (ppm): 1.78–1.86 (m, 1H, SH); 2.20–2.89 (m, 5I, CH$_2$—CH—CH$_2$); 2.95–3.26 (m, 2H, CH$_2$-pyridyl); 4.64–4.75 (m, 1H, CHCOO); 8.33 (d, 1H, JHH=8.1 Hz, NH); 7.10–8.47 (m, 9H, aromatic); 12.7 (bs, 1H, COOH).

EXAMPLE 3

In Vitro Evaluation of the Pharmacologic Activity a) NEP-inhibitory Activity

The NEP-inhibitory activity was evaluated in rat kidney cortex membranes prepared according to the procedure described by T. Maeda et al. in Biochim Biophys. Acta 1983, 731(1), 115–120.

Kidneys were removed from male Sprague-Dawley rats weighing approximately 300 g and kept at 4° C.

Kidney cortex was carefully removed, finely minced and suspended into a homogenization buffer (10 mM sodium phosphate pH 7.4 containing 1 mM MgCl$_2$, 30 mM NaCl, 0.02% NaN$_3$) 1:15 weight/volume.

The tissue was then cold homogenized for 30 seconds using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for the storage of aliquots at −80° C. until use.

The NEP-inhibitory activity was evaluated according to the method described by C. Llorens et aL, in Eur. J. Pharmacol., 69, (1981), 113–116, as reported hereinafter.

Aliquots of the membrane suspension prepared as above described (concentration 5 μg/ml of proteins) were preincubated in the presence of an aminopeptidase inhibitor (Bestatin—1 mM) for 10 minutes at 30° C. [$^3$H][Leu$^5$]-enkephaline (15 nM) and buffer TRIS/HCl pH 7.4 (50 mM) were added in order to obtain a final volume of 100 μl.

The enzymatic reaction was stopped by adding HCl 0.1M (100 μl) after 20 minutes of incubation at 30° C.

The formation of the metabolite [$^3$H]Tyr-Gly-Gly was quantified, after separation of the unreacted substrate by chromatography on polystyrene columns (Porapak Q), by measuring the relative radioactivity through liquid scintillation.

The percentage of inhibition of the metabolite formation in the membrane preparations treated with the compounds of formula I and with the comparative compounds with respect to the untreated membrane preparations was expressed as IC$_{50}$ (nM) value.

b) ACE-inhibitory Activity

The ACE-inhibitory activity was evaluated according to the method reported in the literature by B. Holmquist et al., in Analytical Biochemistry 95, 540–548 (1979).

50 μM of ACE (250 μmU/ml purified by lung rabbit, EC 3.4.15.1 SIGMA) were preincubated with 50 μl of the compound of formula I or of the comparison compound or related vehicle in thermostated cuvettes at 37° C.

The reaction was started by adding 500 μl of furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curyes, the absorbance at 340 nm was recorded in continuo for 5 minutes.

The percentage of inhibition in the preparations incubated with the compounds of formula I or with the comparative compounds with respect to the preparations incubated with the vehicle was expressed as IC$_{50}$ (nM) value.

We report in the following table 1 the IC$_{50}$ (nM) values related to the ACE-inhibitory and NEP-inhibitory activity of the compounds 4, 5 and 6 and of the comparison compounds Thiorphan and Captopril.

TABLE 1

ACE-inhibitory and NEP-inhibitory activity, expressed as IC$_{50}$ (nM), of compound 4, of compound 5, of compound 6, of Thiorphan and of Captopril.

| Compound | ACE-inhibitory activity IC$_{50}$ (nM) | NEP-inhibitory activity IC$_{50}$ (nM) |
|---|---|---|
| 4 | 12 | 4.7 |
| 5 | 6.5 | 5.5 |
| 6 | 23 | 7.1 |
| Thiorphan | 99 | 18 |
| Captopril | 4.6 | not active |

The data reported in table 1 show that the compounds of formula I, object of the present invention, are endowed with a significant dual ACE/NEP inhibitory activity. Said activity resulted to be comparable to that of CaptopriL to what it concerns the ACE-inhibitory activity, and to that of Thiorphan, to what it concerns the NEP-inhibitory activity.

What is claimed is:

1. A compound of formula

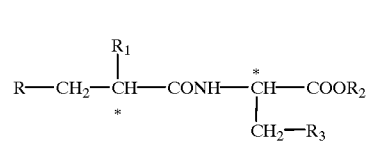

(I)

wherein

R is a mercapto group or a R$_4$COS group convertible in the organism to mercapto group;

R$_1$ is a straight or branched C$_2$–C$_4$ alkyl group or an aryl or arylalkyl group with from 1 to 6 carbon atoms in the alkyl moiety wherein the aryl is a phenyl or a 5 or 6 membered aromatic heterocycle with one or two heteroatoms selected among nitrogen, oxygen and sulphur, optionally substituted with one or more substituents, the same or different, selected among halogen atoms, hydroxy groups, alkoxy, alkyl alkylthio, alkylsuphonyl or alkoxycarbonyl groups with from 1 to 6 carbon atoms in the alkyl moiety, $C_1$–$C_3$ alkyl groups containing one or more fluorine atoms, carboxy groups, nitro groups, amino or aminocarbonyl groups, acylamino groups, aminosulphonyl groups, mono- or di-alkylamino or mono- or di-alkylaminocarbonyl groups with from 1 to 6 carbon atoms in the alkyl moiety;

$R_2$ is a hydrogen atom, a straight or branched $C_1$–$C_4$ alkyl group or a benzyl group;

$R_3$ is a 5 or 6 membered aromatic heterocycle with one or two heteroatoms selected among nitrogen, oxygen and sulphur, optionally substituted with a phenyl group, being the phenyl and the heterocyclic group optionally substituted with one or more substituents, the same or different, selected among halogen atoms, alkyl alkoxy, alkylthio or alkoxycarbonyl groups with from 1 to 3 carbon atoms in the alkyl moiety;

$R_4$ is a straight or branched $C_1$–$C_4$ alkyl group or a phenyl group;

the carbon atoms marked with an asterisk are stereogenic centers;

and pharmaceutically acceptable salts thereof;

provided that $R_3$ is not an imidazolyl, furyl, thienyl, benzofuryl, benzothienyl or indolyl group.

2. A compound of formula I according to claim 1 wherein $R_3$ is a 5 or 6 membered aromatic heterocyclic group with one or two heteroatoms selected among nitrogen, oxygen and sulphur.

3. A compound of formula I according to claim 2 wherein $R_1$ is a phenylalkyl group optionally substituted with one or more substituents, the same or different, selected among halogen atoms, hydroxy, alkyl or alkoxy groups.

4. A compound of formula I according to claim 1 in the form of a salt with an alkali metal selected among sodium, lithium and potassium.

5. A process for the preparation of a compound of formula I according to claim 1 comprising the reaction between a compound of formula

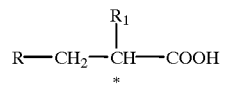

(II)

wherein
R and $R_1$ have the meanings reported in claim 1;
and an alanine derivative of formula

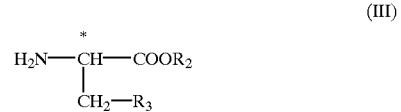

(III)

wherein
$R_2$ and $R_3$ have the meanings reported in claim 1.

6. A pharmaceutical composition comprising a therapeutically effective amount of a compound of formula I according to claim 1 in admixture with a pharmaceutically acceptable carrier.

7. A pharmaceutical composition according to claim 6 for the treatment of cardiovascular diseases in a mammal.

8. A method for the treatment of cardiovascular diseases in a mammal comprising the administration of a therapeutically effective amount of a compound according to claim 1.

9. N-(3-phenylcarbonylthio-2-phenylmethylpropionyl)-(4-thiazolyl)-L-alanine methyl ester.

10. N-(3-phenylcarbonylthio-2-phenyimethylpropionyl)-(2-pyridyl)-L-alanine methyl ester.

11. N-(2-phenylmethyl-3-mercaptopropionyl)-(4thiazoly)-L-alanine.

12. N-(2-phenylmethyl-3-mercaptopropionyl)-(2-pyridyl)-L-alanine.

* * * * *